United States Patent
Newton et al.

(10) Patent No.: US 7,189,244 B2
(45) Date of Patent: Mar. 13, 2007

(54) COMPRESSOR FOR USE IN MINIMALLY INVASIVE SURGERY

(75) Inventors: Peter Newton, San Diego, CA (US); Mark Gracia, Rochester, MA (US); Michael S. Varieur, Portsmouth, RI (US); Carrie A. Breech, Wrentham, MA (US)

(73) Assignee: DePuy Spine, Inc., Raynham, MA (US)

( * ) Notice: Subject to any disclaimer, the term of this patent is extended or adjusted under 35 U.S.C. 154(b) by 526 days.

(21) Appl. No.: 10/256,635

(22) Filed: Sep. 27, 2002

(65) Prior Publication Data

US 2004/0024411 A1 Feb. 5, 2004

Related U.S. Application Data

(60) Provisional application No. 60/400,966, filed on Aug. 2, 2002.

(51) Int. Cl.
  *A61B 17/58* (2006.01)
  *A61B 17/00* (2006.01)
(52) U.S. Cl. ..................... 606/105; 606/205
(58) Field of Classification Search ............... 606/105, 606/205, 206, 207, 208, 209, 99, 86, 167, 606/174, 175; 30/232, 241
See application file for complete search history.

(56) References Cited

U.S. PATENT DOCUMENTS

| | | | | |
|---|---|---|---|---|
| 943,263 | A | * | 12/1909 | Moraweck ................. 606/205 |
| 1,002,961 | A | * | 9/1911 | Beuoy et al. ............... 606/135 |
| 1,085,461 | A | | 1/1914 | Michaelis |
| 4,944,739 | A | | 7/1990 | Torre |
| 5,281,223 | A | | 1/1994 | Ray |
| 5,591,167 | A | | 1/1997 | Laurain et al. |
| 5,591,176 | A | * | 1/1997 | Henderson et al. ......... 606/137 |
| 5,643,316 | A | * | 7/1997 | Kaiser et al. ............... 606/205 |
| 5,702,453 | A | | 12/1997 | Rabbe et al. |
| 5,746,768 | A | * | 5/1998 | Lewis et al. ................ 606/205 |
| 5,810,878 | A | * | 9/1998 | Burel et al. ................. 606/205 |
| 5,997,565 | A | * | 12/1999 | Inoue ......................... 606/205 |
| 6,099,528 | A | | 8/2000 | Saurat |
| 6,102,912 | A | | 8/2000 | Cazin et al. |
| 6,261,296 | B1 | | 7/2001 | Aebi et al. |

FOREIGN PATENT DOCUMENTS

CH 662 937 A5 11/1987

* cited by examiner

*Primary Examiner*—Pedro Philogene
(74) *Attorney, Agent, or Firm*—Nutter, McClennen & Fish, LLP

(57) ABSTRACT

A compressor tool for use in minimally invasive surgery is provided having first and second elongate elements where each elongate element is connected to the other at a pivot point within a pivot region of each element for rotating articulation in an articulation plane with respect to each other. The first and second elongate elements are configured to provide a tool pivot region including the pivot point, a tool handle proximal to the tool pivot region, and a tool working portion distal to the too pivot region so that pressure applied to the tool handle portion results in a compressive force being applied by the tool working portion. The tool has a first closed position for insertion of the tool through an incision or portal so that the pivot region is located within the incision or portal, and a second working position where the tool working portion is arranged to provide a compressive force to spaced apart elements within a patient's body. Articulation of the tool between the first closed position and the second working position results in no increase in dimension of the tool in the pivot region.

9 Claims, 5 Drawing Sheets

COMPRESSOR FOR USE IN MINIMALLY INVASIVE SURGERY

RELATED APPLICATIONS

This application claims priority to provisional application U.S. Ser. No. 60/400,966, filed Aug. 2, 2002.

FIELD OF THE INVENTION

The present invention relates to devices and systems for compressing a patient's spine between fixation screws in a spinal fixation construct. More particularly, the invention provides a compressor tool for use in minimally invasive surgery having a small cross section and a pivot region that remains smaller than the minimally invasive surgery entry site regardless of the state of the compressor tool.

BACKGROUND OF THE INVENTION

The use of spinal fixation instrumentation to align and/or fix a desired relationship between adjacent vertebral bodies is well established. Such instrumentation typically includes a spinal fixation element, such as a relatively rigid fixation rod, that is coupled to adjacent vertebrae by attaching the element to screws which have been inserted into the patient's vertebrae or to spinal hooks which can be placed into a vertebral arch for coupling to the vertebral bodies. Once installed, the spinal fixation instrumentation holds the vertebrae in a desired spatial relationship, either until desired healing or spinal fusion has taken place, or for some longer period of time.

One example of a rod based spinal fixation system is provided in U.S. Pat. No. 5,005,562, issued Apr. 9, 1991 to Cotrel (which is hereby incorporated by reference). This system includes pedicle screw and spinal hook vertebral coupling elements having integral U-shaped bodies that extend outward from the vertebrae to which they are attached. A spinal fixation rod is shaped as desired and fitted into the "U" of U-shaped bodies of adjacent vertebrae. The inner surfaces of the U-shaped body are threaded to accept a set screw, and rod is fixed to the vertebral coupling elements by threading a set screw into each of the U-shaped bodies to lock in the rod.

U.S. Pat. No. 5,545,165, issued Aug. 13, 1996 to Biedermann et al. (and incorporated herein by reference), illustrates an improvement in closure systems for fixing a rod to vertebral coupling elements over those provided by Cotrel. The Biedermann et al. system also uses pedicle screws and spinal hooks having U-shaped bodies that extend outward from the vertebrae to which they are attached. The U-shaped bodies of the Biedermann et al. system are threaded on both the inside and the outside. The rod is therefore locked in by both an inner set screw and an outer lock nut. In the illustrated embodiments, the inner set screw is adapted to be driven on its threads using a hex-shaped driver element, and the outer locking nut is provided with hex-shaped flat outer surfaces suitable for engagement with a wrench or similar driving tool.

When using screws and rods in spinal surgery, compression between the screws is often desired, or even required. For some procedures, compression of the spine between screws can help to conform the spine to a desired profile (such as when correcting a scoliotic spine). For many procedures, compression is desired to place a load on bone graft material that has been loaded into the disc space in order to promote healing and rapid fusion. In response to this need, conventional compressor tools have been developed. These conventional compressor tools can be generally shaped like a common pair of pliers, specially adapted to contact screws placed in adjacent vertebrae so that a surgeon can squeeze the handle portion of the conventional compressor tool to compress a region of the spine being treated.

Many surgeons are now treating spinal pathologies (spondylolysis, degenerative disc disease, scoliosis, etc.) through smaller and smaller incisions or portals (an approach commonly known as minimally invasive surgery). For example, many surgeons now prefer to treat anterior spinal deformities thoroscopically. In order to accomplish surgery in this manner, each of the instruments used in the surgery must be designed to fit into either the incision or portal and be articulated with minimal trauma to the surgical site. Conventional compressor tools include pivot regions that grow in dimension about the pivot when the tool is articulated. This makes conventional compressor tools unusable in minimally invasive surgery.

In an attempt to overcome this problem, one style of compressor has been designed to have a rack and pinion system. This system is inserted into the surgical site so that the pinion may be articulated with a tool such as a screwdriver. Still another style of compressor uses a cable system that is wrapped around the implanted screws. By increasing tension on the cable, compression is created. Each of these designs has its own set of problems however, including the amount of time it takes to set up and use the tools, and the extra mechanical advantage that the tools provide. Extra mechanical advantage can be a problem in that surgeons must learn how much force is applied by the device, as opposed to force provided by the surgeon, so that the surgeon can be careful not to apply too much compression.

Accordingly, a need exists for a compressor tool for surgeons who choose to perform spinal fixation surgery using minimally invasive techniques and without the problems of known compressor tools.

SUMMARY OF THE INVENTION

The present invention provides a compression tool for use in minimally invasive surgery that maintains a narrow pivot region throughout its operation so that it may be placed into a minimally invasive incision or portal and be used during surgery without interference with the incision or portal. In a first aspect of the invention, the tool has first and second elongate elements where each elongate element is connected to the other at a pivot point within a pivot region of each element for rotating articulation in an articulation plane with respect to each other. The first and second elongate elements are configured to provide a tool pivot region including the pivot point, a tool handle proximal to the tool pivot region, and a tool working portion distal to the tool pivot region so that pressure applied to the tool handle portion results in a compressive force being applied by the tool working portion. The tool has a first closed position for insertion of the tool through an incision or portal so that the pivot region is located within the incision or portal, and a second working position where the tool working portion is arranged to provide a compressive force to spaced apart elements within a patient's body. Articulation of the tool between the first closed position and the second working position results in no increase in dimension of the tool in the pivot region.

In a further aspect of the invention, a compression tool for use in minimally invasive surgery is provided having first and second elongate elements where each elongate element includes a pivot region, a handle portion proximal to the pivot region, and a working portion distal to the pivot region. Each elongate element is connected to the other at a pivot point within the pivot region of each element for rotating articulation in an articulation plane with respect to each other so that pressure applied to the first and second elongate element handle portions toward each other results in a compressive force being applied by the compressor tool at respective distal ends of the first and second elongate element working portions. The compressor tool defines a tool longitudinal axis and, for the first elongate element, the working portion is offset from the pivot region in a direction that is transverse to the tool longitudinal axis and opposed to an articulation direction of the second elongate element and the working portion extends distally from the pivot region at an angle such that when the pivot region is aligned with the tool longitudinal axis, the working portion extends distally in a direction away from the tool longitudinal axis and opposed to the articulation direction of the second elongate element.

In a further embodiment, a compressor tool of the invention as described above can be configured to have a first closed position for insertion of the compressor tool through an incision or portal wherein the first and second elongate element working portions are proximate to the tool longitudinal axis, and a second working position wherein the first and second working portions are spaced apart. The tool can further be configured so that articulation of the tool between the first and second positions results in no increase in dimension of the tool in a tool pivot region including the pivot point of each elongate member.

In a more detailed embodiment, the tool can further be configured so that in the first closed position, and for the first elongate element, the handle portion extends proximally from the pivot region on a first side with respect to the tool longitudinal axis in the articulation plane. A first offset region can then extend between the pivot region and the handle region; the first offset region extending across the longitudinal axis to an opposed second side of the longitudinal axis in the articulation plane as it connects these elements. The pivot region can then extend from the first offset region on the second side across the longitudinal axis at the pivot point to the first side and a second offset region next extends from a distal end of the pivot region on the first side across the longitudinal axis to the second side and the working portion extends distally from the second offset region on the second side. The second elongate element can further be a mirror image of the first elongate element.

BRIEF DESCRIPTION OF THE DRAWINGS

The invention will be more fully understood from the following detailed description taken in conjunction with the accompanying drawings.

DETAILED DESCRIPTION OF THE INVENTION

The present invention provides a compression tool providing the benefits of known compression tools for use in spinal fixation surgery, but also having a smaller profile, especially in a pivot region of the tool, so that the tool may be effectively used in minimally invasive surgery. Another feature of at least one embodiment of the invention is that the pivot region of the compression tool maintains its cross-sectional dimensions as the tool is articulated between open and working positions so that in use, the tool may be placed for operation so that the pivot region is located within the incision or portal used for the surgery and may be operated without constraints arising from the dimensions of the incision or portal.

Figure 1:
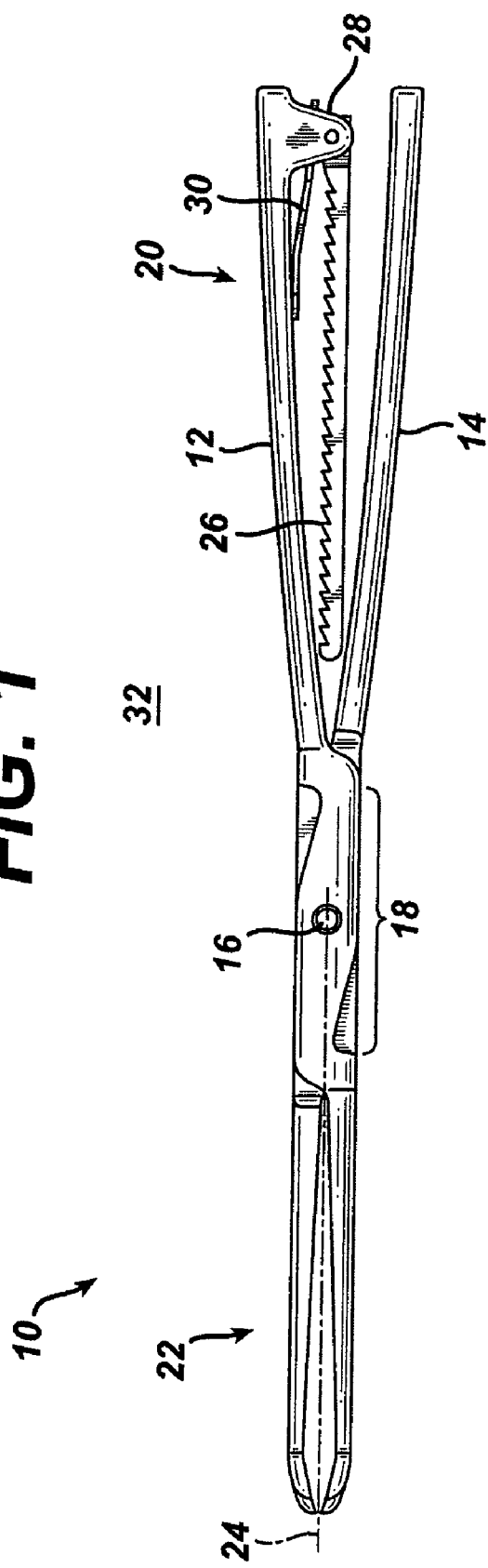
FIG. 1 a side view of a compression tool of the invention.
Figure 2:
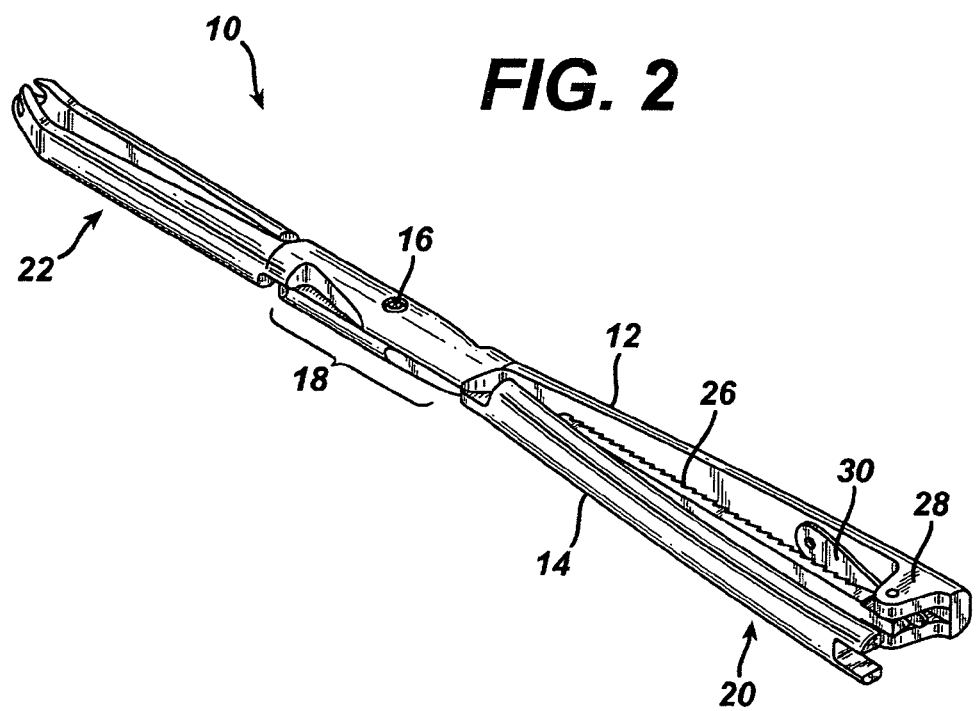
FIG. 2 is an isometric view of the compression tool of FIG. 1.

As illustrated in side and perspective views in FIGS. 1 and 2, respectively, a compressor tool 10 of the invention comprises first 12 and second 14 elongate members rotatably connected at pivot point 16. Tool 10, having a tool longitudinal axis 24, can be divided into a tool pivot region 18 which includes pivot point 16, a tool handle 20 extending proximally from the pivot region, and a tool working portion 22 extending distally from the pivot region. Compressor tool 10 can be operated by articulating the tool handle 20 to place the elongate members 12, 14 substantially along tool longitudinal axis 24 in a closed position of the tool (the position illustrated in FIGS. 1 and 2) in which the tool has its smallest cross-sectional dimensions along the tool working portion 22 and tool pivot region 18 so that the tool may be inserted into a patient through an incision or portal up to the pivot region of the tool. In one preferred embodiment, the tool will fit through an opening of less than or equal to about 20 millimeters in this way. In a further embodiment, the tool will fit through an opening of about 15 millimeters. The plane defined by the articulation motion of tool handle 20 and tool working portion 22 can be referred to as articulation plane 32 (the plane represented by the drawing sheet in FIG. 1) which includes tool longitudinal axis 24.

Figure 5:
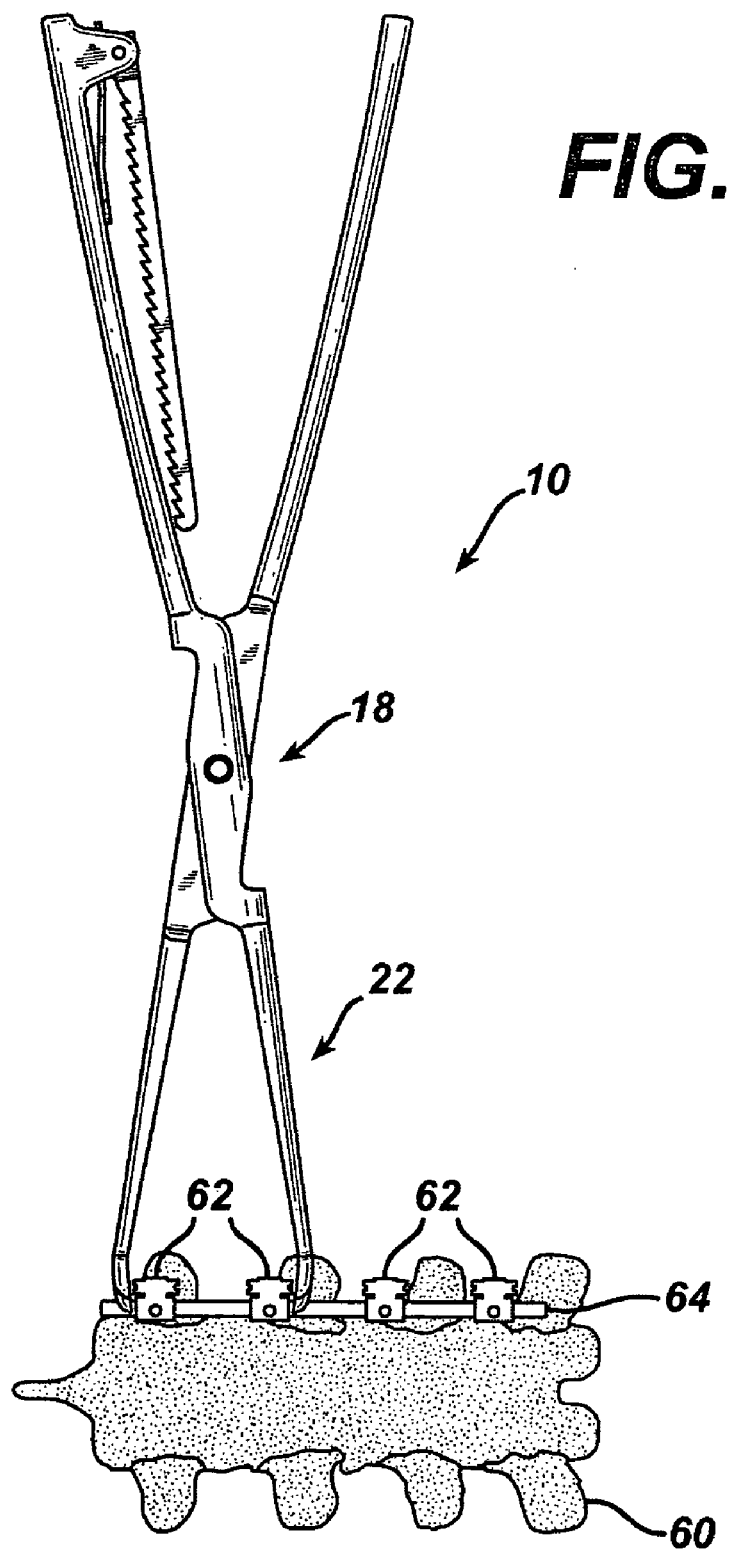
FIG. 5 is a side view of the compression tool of FIGS. 1 and 2 in use in a second working position.

Tool handle 20 can also be articulated to spread apart the elements of the tool working portion 22 to grasp elements of the patient's body or implanted elements attached to the patient's body so that squeezing the tool handle applies compression to the elements grasped (this position is illustrated in FIG. 5). Tool 10 of the invention can provide at least two significant advantages over many known tools. First, the tool can be articulated between its open and closed positions without expansion of dimension in tool pivot region 18. In this way, once the tool is inserted into the patient so that tool pivot region 18 is located in the incision or portal, the tool can be articulated between its open and closed positions without interference from the minimally invasive incision or port. Secondly, tool 10 provides little or no mechanical advantage other than that provided by the lengths of tool handle 20 portions which act as levers. The advantage to providing no further mechanical advantage is that a surgeon can develop a feel for the amount of compression the surgeon wishes to provide and feedback to the surgeon through the tool handle will tell the surgeon when the desired amount of compression has been achieved.

Tool 10 can also include a ratchet bar 26 rotatably connected to a ratchet bar connecting element 28 on first elongate element 12. As a person of ordinary skill in the art will readily recognize, ratchet bar 26 can be used to lock the position of tool handle 20 against releasing compression that has been applied. A ratchet bar spring 30 can also be provided to encourage sustained contact between ratchet bar 26 and the relevant portions of tool handle 20.

A more complete understanding of an exemplary tool geometry that allows the dimensional advantages of the compression tool of the invention can be gained by reference to the side view of first elongate element 12 provided in FIG.

3. First elongate element 12 includes a first element pivot region 34 that includes pivot point 16. In one embodiment, pivot region 34 extends approximately 30 millimeters in each direction along tool longitudinal axis 24 from pivot point 16. First elongate element 12 includes a first element handle portion 36 that extends proximally from pivot region 34 on a first side 38 with respect to tool longitudinal axis 24 in articulation plane 32. A first offset region 40 exists between pivot region 34 and handle portion 36 and extends across longitudinal axis 24 to an opposed second side 42 of longitudinal axis 24 in articulation plane 32 with pivot region 34 extending from first offset region 40 on the second side 42 across longitudinal axis 24 at pivot point 16 to the first side 38.

A second offset region 44 extends from a distal end of pivot region 34 on the first side 38 across longitudinal axis 24 to second side 42, and a working portion 46 of first elongate element 12 extends distally from second offset region 44 on second side 42. The distal end 48 of working portion 46 can be curved toward longitudinal axis 24 so as to make it easier to insert the compressor tool into the patient during minimally invasive surgery. Distal end 48 can also be curved in other directions or shaped as desired in order to provide the desired compression.

In an exemplary embodiment, first and second offset regions 40, 44 extend approximately 10 millimeters in a longitudinal direction and working portion 46 extends approximately 100 millimeters beyond second offset region 44.

Figure 3:
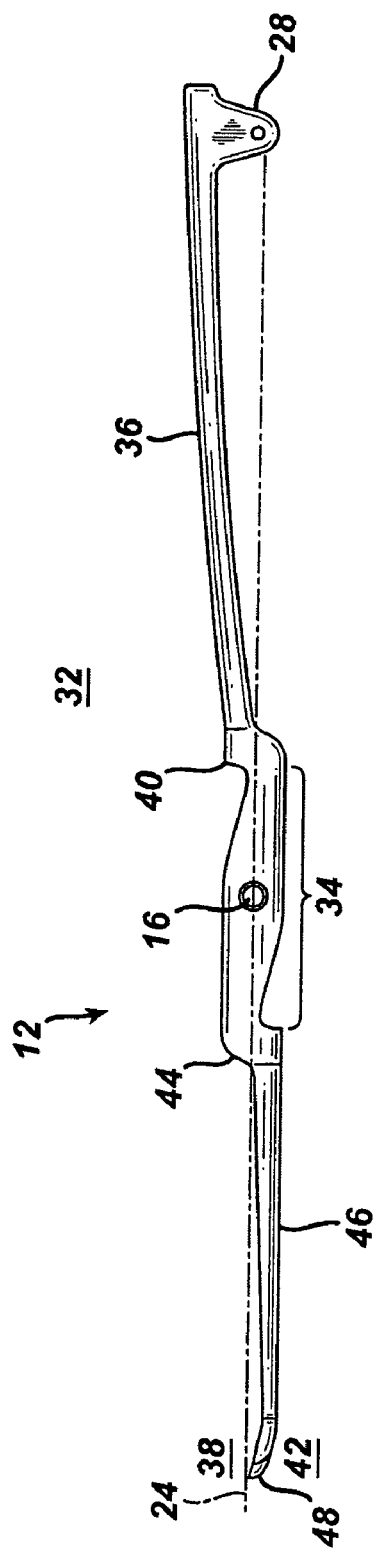
FIG. 3 is a side view of a first elongate element of the compression tool of FIGS. 1 and 2.

The shape of pivot region 34 can also be configured to provide the desired dimensional features of the invention. As illustrated in FIG. 3, on either side of pivot point 16, the sides of pivot region 34 can curve or bend inward. In addition, pivot region 34, as well as first and second offset regions 40, 44 can have a "D" shaped cross section, with the flat side of the D facing the second elongate member (this can best be seen by reference to FIG. 2). In this way, when the second elongate member is shaped similarly to first elongate member 12, pivot region 34 can fit within a cylinder of minimized diameter (15 millimeters in an exemplary embodiment) as the tool is being articulated between its closed and working positions.

In a preferred embodiment, second elongate element 14 is a mirror image of first elongate element 12 and having substantially the same dimensions except that second elongate element 14 does not have a ratchet bar connecting element. This embodiment is illustrated in each of FIGS. 1, 2, 4 and 5.

Figure 4:
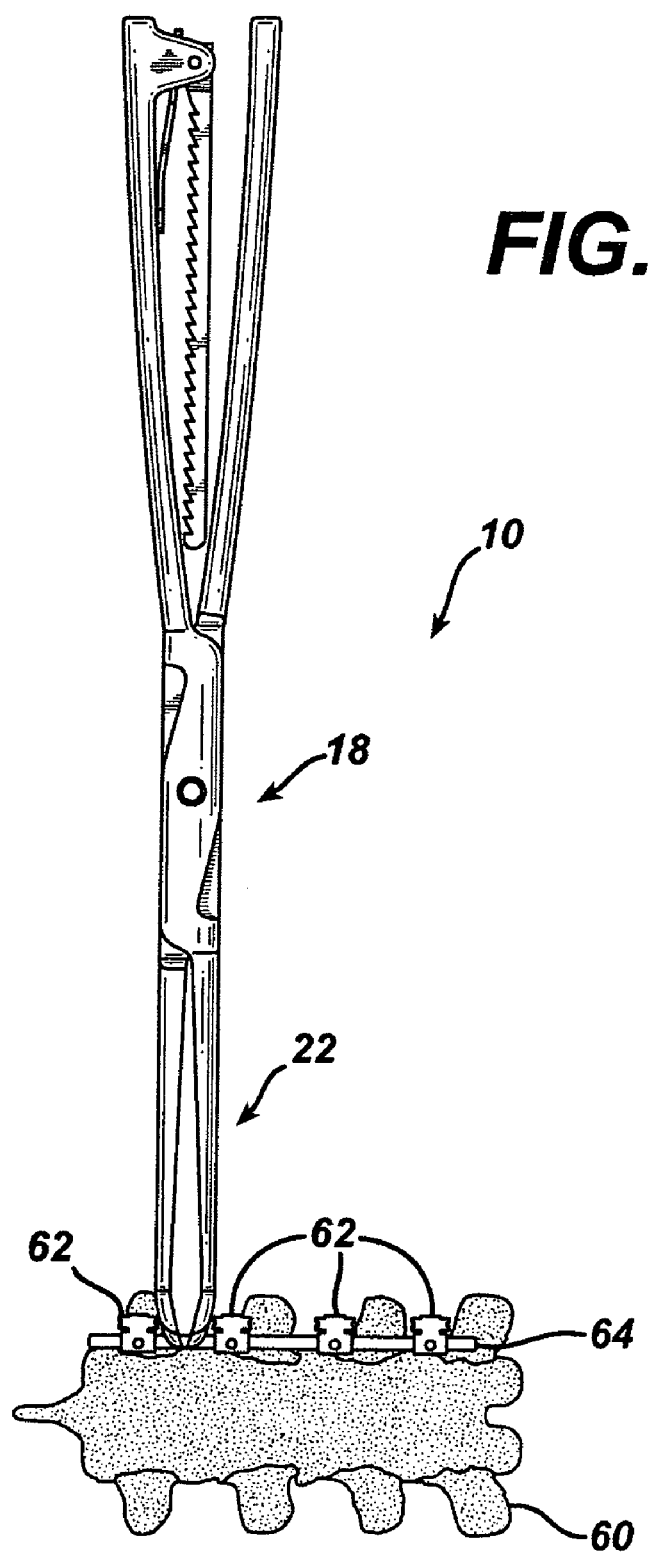
FIG. 4 is a side view of the compression tool of FIGS. 1 and 2 in use in a first closed position.

The operation and advantages of the invention can further be seen by reference to FIGS. 4 and 5. In FIG. 4, compressor tool 10 of the invention is in its closed position and has been inserted into a patent's body to operate on a patient's spine 60 having rod receiving screws 62 attached thereto, one each to a vertebrae, with a spinal fixation rod 64 provisionally placed in the rod receiving screws 62. While not shown in the figure, compressor tool 10 is sized so that tool pivot region 18 is located within the incision or portal through which the procedure is being performed. In the illustrated position, both tool working portion 22 and tool pivot region 18 will fit through the incision or portal, which, in one embodiment, can be sized as less than or equal to approximately 20 millimeters, or in one embodiment, about 15 millimeters across.

Turning to FIG. 5, compressor tool 10 has been articulated from its closed position to its working position and the tool working portion 22 positioned to compress two vertebrae by applying a compressive force to the rod receiving screws 62 implanted in those vertebrae. Despite the fact that tool working end 22 has been expanded to apply a compressive force against two surfaces that are at least about 20 millimeters apart, tool pivot region 18 maintains is cross sectional dimensions less than or equal to the dimension of the incision or portal, which, in this embodiment is approximately 15 millimeters.

A person of ordinary skill in the art will appreciate further features and advantages of the invention based on the above-described embodiments. By way of example, the compression tool of the invention could be used with vertebral coupling elements such as mono-axial pedicle screws (see, e.g., FIGS. 1 to 4 of U.S. Pat. No. 5,725,527 to Biedermann et al. which is incorporated herein by reference) or spinal hooks (see, e.g., FIG. 5 of Biedermann et al.). Accordingly, the invention is not to be limited by what has been particularly shown and described, except as indicated by the appended claims. All publications and references cited herein are expressly incorporated herein by reference in their entity.

What is claimed is:

1. A compressor tool for use in minimally invasive surgery, comprising:
   first and second elongate elements, each elongate element
      having
      a pivot region,
      a handle portion proximal to the pivot region, and
      a working portion distal to the pivot region,
   each elongate element being connected to the other at a pivot point within the pivot region of each element for rotating articulation in an articulation plane with respect to each other so that pressure applied to the first and second elongate element handle portions toward each other results in a compressive force being applied by the compressor tool at respective distal ends of the first and second elongate element working portions;
   wherein the compressor tool defines a tool longitudinal axis and, for the first elongate element, the working portion is offset from the pivot region in a direction that is transverse to the tool longitudinal axis and opposed to an articulation direction of the second elongate element end the working portion extends distally from the pivot region at an angle such that when the pivot region is aligned with the tool longitudinal axis, the working portion extends distally in a direction away from the tool longitudinal axis and opposed to the articulation direction of the second elongate element and
   wherein the compressor tool is configured to have a first closed position for insertion of the compressor tool through an incision or portal wherein the first and second elongate element working portions are proximate to the tool longitudinal axis, and a second working position wherein the first and second working portions are spaced apart, and wherein articulation of the tool between the first and second positions results in no increase in dimension of the tool in a tool pivot region including the pivot point.

2. The tool of claim 1, wherein in the first closed position for the first elongate element, the first element handle portion extends proximally from the pivot region on a first side with respect to the tool longitudinal axis in the articulation plane, a first offset region between the pivot region and the handle region extends across the longitudinal axis to an opposed second side of the longitudinal axis in the articulation plane, the pivot region extends from the first offset region on the second side across the longitudinal axis at the pivot point to the first side, a second offset region extends from a distal end of the pivot region on the first side across the longitudinal axis to the second side, and the working portion extends distally from the second offset region on the second side.

3. The tool of claim 1, wherein for the second elongate element, the working portion is offset from the pivot region in a direction that is transverse to the tool longitudinal axis and opposed to an articulation direction of the first elongate element and the working portion extends distally from the pivot region at an angle such that when the pivot region is aligned with the tool longitudinal axis, the working portion extends distally in a direction away from the tool longitudinal axis and opposed to the articulation direction of the first elongate element.

4. The tool of claim 2, wherein the second elongate element is a mirror image of the first elongate element.

5. The tool of claim 1, wherein the tool pivot region extends along the tool longitudinal axis.

6. The tool of claim 1, wherein the tool pivot region extends at least about 30 millimeters along the tool longitudinal axis.

7. The tool of claim 5, wherein the tool pivot region maintains a dimension of not more than about 20 millimeters.

8. The tool of claim 1, wherein the tool working end expands to operate to compress surfaces spaced at least about 20 millimeters apart.

9. The tool of claim 1, wherein the tool pivot region is located between the offset working portions of the elongate elements.

* * * * *